United States Patent [19]
Lee et al.

[11] Patent Number: 5,288,615
[45] Date of Patent: Feb. 22, 1994

[54] METHODS FOR PREPARING PROTEINS OF ALTERED STRUCTURE

[75] Inventors: Annette T. Lee, New York; Anthony Cerami, Shelter Island, both of N.Y.

[73] Assignee: The Rockefeller University, New York, N.Y.

[21] Appl. No.: 864,523

[22] Filed: Apr. 7, 1992

Related U.S. Application Data

[60] Continuation of Ser. No. 499,885, Mar. 27, 1990, abandoned, which is a continuation of Ser. No. 144,404, Jan. 15, 1988, abandoned, which is a continuation-in-part of Ser. No. 885,967, Jul. 15, 1986, Pat. No. 4,761,368, which is a division of Ser. No. 590,820, Mar. 19, 1984, Pat. No. 4,665,192, and a continuation-in-part of Ser. No. 97,856, Sep. 17, 1987, abandoned.

[51] Int. Cl.$^5$ .................. C12N 15/00; C12N 15/09; C12P 21/00
[52] U.S. Cl. .................. 435/69.1; 435/71.1; 435/71.2; 435/170; 435/172.1; 435/172.3; 935/9; 935/10
[58] Field of Search ............ 435/71.1, 71.2, 170, 435/172.1, 172.3, 69.1; 935/9, 10

[56] References Cited

PUBLICATIONS

Bucala et al., Proc. Natl. Acad. Sci. USA, 81, pp. 105–109 (1984).
Bucala et al., Proc. Natl. Acad. Sci. USA, 82, pp. 8439–8442 (1985).
Lee et al., Mutation Research, 179, pp. 151–158 (1987).
Lee et al., Age, 10, pp. 150–155 (1987).
Lee et al., Proc. Natl. Acad. Sci. USA, 84, pp. 8311–8314 (1987).

*Primary Examiner*—Robert A. Wax
*Assistant Examiner*—Rebecca Prouty
*Attorney, Agent, or Firm*—Klauber & Jackson

[57] ABSTRACT

The present invention relates to methods for inducing cellular mutation by promoting the reaction of nonenzymatic glycosylation of genetic material, such as DNA and RNA, by incubation of the genetic material with certain protein structure modifying agents. Suitable such agents are reducing sugars, such as glucose, glucose-6-phosphate and a reactive intermediate comprising a complex between glucose 6-phosphate and lysine. The methods include the in vitro reaction of the agent with genetic material, such as a particular gene-bearing plasmid, under conditions promoting mutation followed by the introduction of the plasmid bearing the reacted gene into a host cell, and allowing the reacted gene to be mutated and expressed, after which the mutant protein of interest may be isolated. In a variation on the last-mentioned method, a first genetic material may be incubated with the agent and reacted, and this reacted genetic material may then be introduced into a distinct cellular strain and appropriately incubated whereupon the first reacted genetic material will cause the mutation of the genetic material in the distinct cellular strain. The invention also includes an in vivo embodiment wherein the particular genetic material of interest may be isolated and introduced into a host cell which contains high intracellular concentrations of the protein structure modifying agent(s). In this instance, the mutation is promoted by the host cell, and the mutant material may thereafter be isolated and recovered. Diagnostic methods employing the principles of the invention are also disclosed.

19 Claims, 6 Drawing Sheets

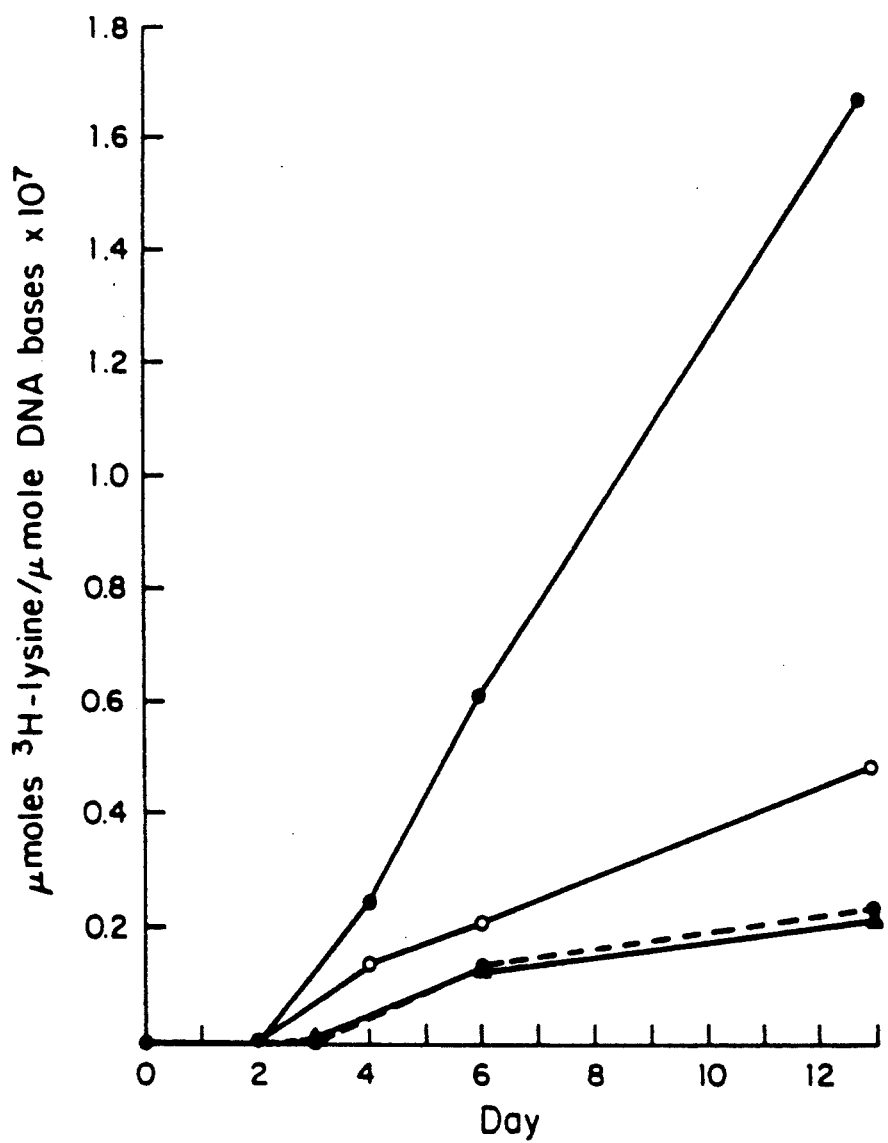
F I G. 1

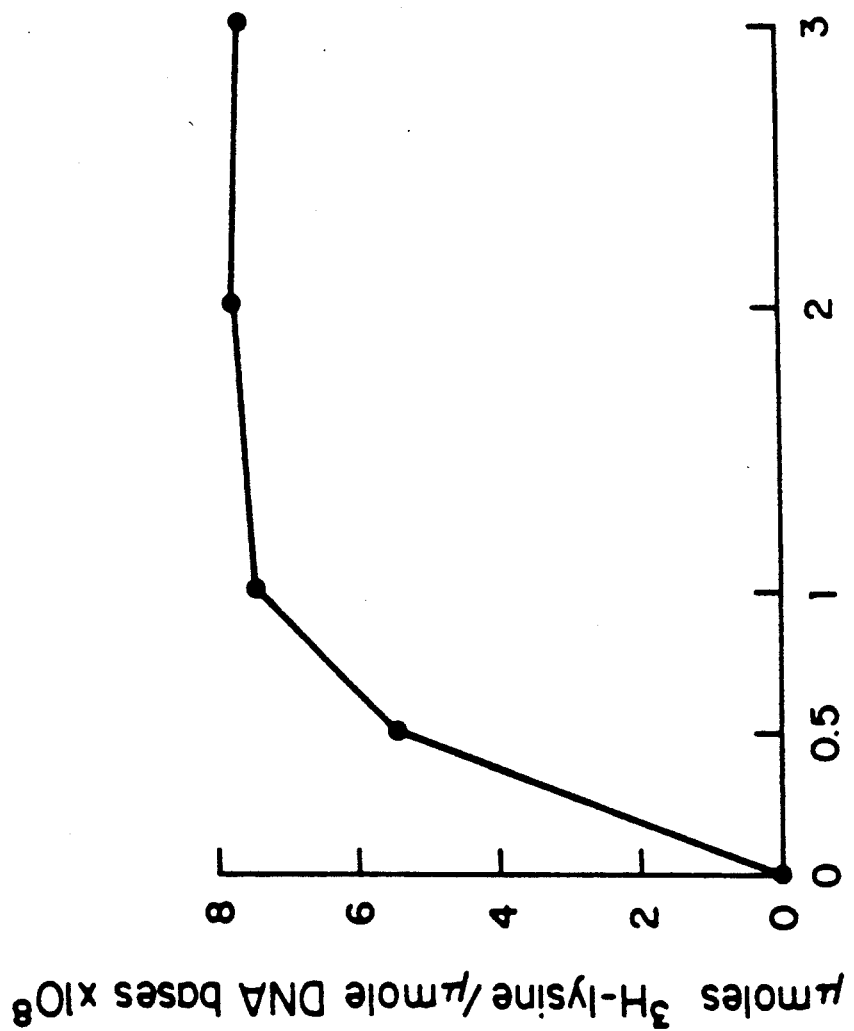

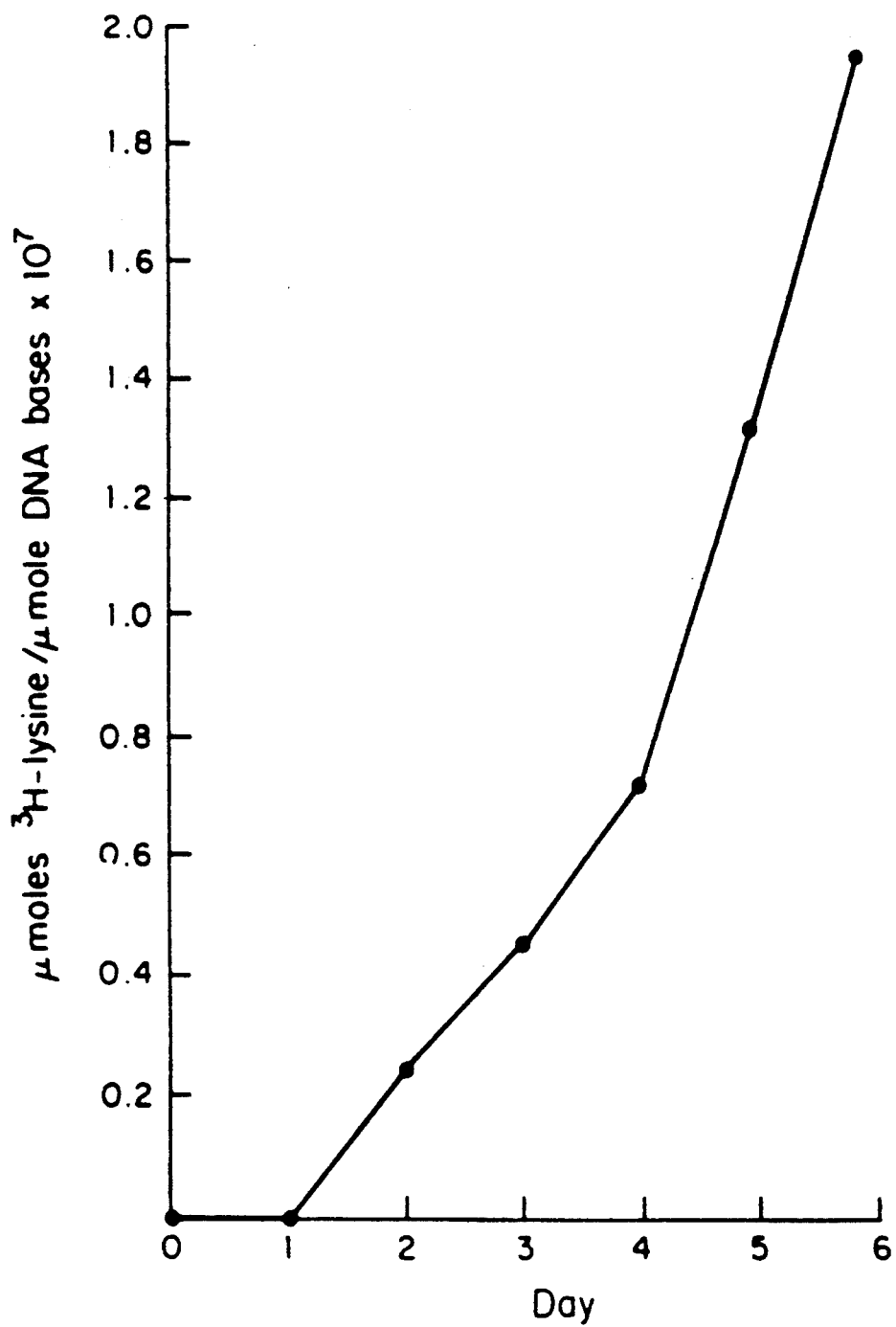
F I G. 2B

METHODS FOR PREPARING PROTEINS OF ALTERED STRUCTURE

This invention was made with partial assistance from grants from the National Institutes of Health, the Brookdale Foundation, and the National Science Foundation.

CROSS REFERENCE TO RELATED APPLICATIONS

This application is a continuation of application Ser. No. 07/499,885, filed Mar. 27, 1990, now abandoned, which is a continuation of application Ser. No. 07/144,404, filed Jan. 15, 1988, now abandoned; which is a continuation-in-part of application Ser. No. 885,967 filed Jul. 15, 1986 now U.S. Pat. No. 4,761,368, which is in turn a division of application Ser. No. 590,820 filed Mar. 19, 1984, now U.S. Pat. No. 4,665,192 issued May 12, 1987, both by Anthony Cerami, one of the inventors herein. The present application is also a continuation in part of application Ser. No. 097,856, now abandoned filed Sep. 17, 1987, by James G. Farmar, Peter Ulrich and Anthony Cerami. The disclosures of all prior applications are incorporated herein by reference.

RELATED PUBLICATIONS

The Applicants are co-authors of the following articles directed to the subject matter of the present invention: "The Formation of Reactive Intermediate(s) of Glucose 6-phosphate and Lysine capable of Rapidly Reacting with DNA." Mutation Res., Vol. 179, pp. 151-158 (1987); "Elevated Glucose 6-phosphate Levels are Associated with Plasmid Mutations in vivo," PROC. NAT. ACAD. SCI. U.S.A., Vol. 84, pp. 8311-8314 (1987), incorporated herein by reference.

BACKGROUND OF THE INVENTION

1. Field of the Invention

The present invention is directed generally to the reaction that occurs between glucose and proteins, and more specifically to the identification of the reaction between reducing sugars and amino acids or proteins with nuclear material (DNA), and the application of this reaction to the synthesis of proteins of altered structure.

2. Description of the Prior Art

The reaction between glucose and proteins has been known for some time. Its earliest manifestation was in the appearance of brown pigments during the cooking of food, which was identified by Maillard in 1912, who observed that glucose or other reducing sugars react with amino acid to form adducts that undergo a series of dehydrations and rearrangements to form stable brown pigments. Maillard, L. C. (1912) C.R. Acad. Sci., Vol. 154, pp. 66-68.

In the years that followed the initial discovery by Maillard, food chemists studied the hypothesized reaction in detail and determined that stored and heat treated foods undergo nonenzymatic browning as a result of the reaction between glucose and the polypeptide chain, and that the proteins are resultingly crosslinked and correspondingly exhibit decreased bioavailability. Finot, P. A. (1982) in Modification of Proteins, eds, Feeney, R. E. and Whitaker, J. R., American Chemical Society, Vol. 198, pp. 91-124, Washington, D.C. At this point, it was determined that the pigments responsible for the development of the brown color that develops as a result of protein glycosylation possessed characteristic spectral properties; however, the chemical structure of the pigments had not been specifically elucidated.

The reaction between reducing sugars and proteins discussed above was found in recent years to have its parallel in vivo. Thus, the nonenzymatic reaction between glucose and the free amino groups on proteins to form a stable 1-amino-1-deoxy-2-ketosyl adduct, known as the Amadori product, has been shown to occur with hemoglobin, wherein a rearrangement of the amino terminal of the beta-chain of hemoglobin by reaction with glucose, forms the adduct known as hemoglobin $A_{1c}$. This reaction was also found to occur with a variety of other body proteins, such as lens crystallins, collagen and nerve proteins. See, Bunn, H. F., Haney, D. N., Gabbay, K. H. and Gallop, P. H. (1975) Biochem. Biophys. Res. Comm. Vol. 67, pp. 103-109; Koenig, R. J., Blobstein, S. H. and Cerami, A. (1977) J. Biol. Chem. Vol. 252, pp. 2992-2997; Monnier, V. M. and Cerami, A. (1983) in *Maillard Reaction in Food and Nutrition*, ed. Waller, G. A., American Chemical Society, Vol. 215, pp. 431-448; and Monnier, V. M. and Cerami, A., (1982) Clinics in Endocrinology and Metabolism Vol. 11, pp. 431-452. Moreover, brown pigments with spectral and fluorescent properties similar to those of late-stage Maillard products have also been observed in vivo in association with several long-lived proteins, such as lens proteins and collagen from aged individuals. An age related linear increase in pigment was observed in human dura collagen between the ages of 20 to 90 years. See, Monnier, V. M. and Cerami, A. (1983) *Biochem. Biophys. Acta.*, Vol. 760, 97-103 (1983); and, Monnier, V. M., Kohn, R. R. and Cerami, A. "Accelerated Age-Related Browning of Human Collagen in Diabetes Mellitus", (1983) *Proc. Nat. Acad Sci.* 81, 583-7. Interestingly, the aging of collagen can be mimicked in vitro by the crosslinking induced by glucose; and the capture of other proteins and the formation of adducts by collagen, also noted, is theorized to occur by a crosslinking reaction, and is believed to account for the observed accumulation of albumin and antibodies in kidney basement membrane. See, Brownlee, M., Pongor, S. and Cerami, A. (1983) *J. Exp. Med.*, 158, 1739-1744 (1983).

As a result of recent studies by one of the inventors herein, further information regarding the chemistry of the late-stage Maillard process has been elucidated, and in particular, certain compounds have been identified that reflect the commencement and existence of the nonenzymatic reaction between proteins and glucose.

Specifically, in patent application Ser. No. 590,820, now U.S. Pat. No. 4,665,192, and in Ser. No. 097,856, filed Sep. 17, 1987, the disclosures of which are both incorporated herein by reference, certain chromophores reflecting these reactions were isolated and found to exist. Of the chromophores identified, the second was found to exist in instances where sulfite inhibition of the Maillard reaction had taken place. The existence of both chromophores confirmed generally the occurrence of nonenzymatic glycosylation of proteins, and specifically, the occurrence of advanced nonenzymatic glycosylation, and prompted further investigations as to the extent of protein-glucose interactions of this kind.

In this connection, the present inventors investigated the possibility that a similar nonenzymatic glycosylation could take place with genetic material encoding cellular proteins leading to a specific alteration of gene structure. This was prompted inasmuch as the earlier work referenced above had revealed that the Maillard reaction was taking place with several long-lived macromolecules in vivo.

Likewise, certain preliminary investigations by Bucala et al., PROC. NATL. ACAD. SCI. U.S.A. (1984), vol. 1981, pp. 105-109, and (1985), vol. 1982, pp. 8439-8442, investigated the effect of glucose 6-phosphate in causing the nonenzymatic modification of DNA and other nucleotides as measured by changes in spectral and fluorescent properties which were similar to those of other nonenzymatically glycosylated proteins. Following incubation of phage or plasmid DNA with glucose 6-phosphate, decreases in transfection and transformation capacities, respectively, were observed. These reactions appear to have a mutagenic effect, in some instances, resulting in both insertions and deletions in the plasmid DNA sequence and the development of multiple plasmid species from a single transformed cell. These earlier findings, however, were inconclusive as to the exact connection or causation for such phenomena, as it was observed by the investigators that certain of the aberrations noted were possibly attributable to glucose 6-phosphate reaction, however were also expected in the instance where DNA is exposed to other agents that may damage it.

Although both groups of investigators speculated respecting the implications of the glucose 6-phosphate reaction with nucleic acid material, none were certain of the mechanism of operation. Further investigations performed by the inventors herein have revealed additional information respecting the glycosylation of nucleic acids and the consequences thereof that are believed particularly relevant to clarifying the aging process as applied to these molecules and forming the basis for further investigations thereof as well as potential diagnostic and therapeutic applications. It is to these latter aims the present invention is accordingly directed.

SUMMARY OF THE INVENTION

In accordance with the present invention, methods and agents are disclosed for the development of proteins of altered structure without the need for chemical synthesis. Accordingly, and in a first aspect of the present invention, a protein of altered structure may be prepared by incubating a protein structure modifying agent with a target genetic material such as the DNA in a particular plasmid under conditions conducive for promoting the mutation of the genetic material. The reacted genetic material would then be introduced into an appropriate host cell for the mutation of the plasmid and the expression of the mutant gene. Subsequently, the resulting mutant clones could be screened, isolated and recovered.

In a variation of the method just described, a nontarget genetic material (i.e. the genetic material from a separate cell line, or genetic material not coding for a particular protein of interest) may be incubated with the protein structure modifying agent. Thereafter, the reacted nontarget genetic material would be recovered and introduced into a distinct host cell having the genetic material of interest (i.e. the target genetic material) and following incubation under conditions conducive to mutation, mutants of the target host cell could be screened, isolated and recovered, which would bear the alteration in object.

In an embodiment of the invention contemplating in vivo operation, a protein of altered structure may be prepared by introducing the desired gene into a cell that accumulates abnormally high intracellular levels of reducing sugar(s), such as the DF40 and DF2000 strains of E. coli. These strains of E. coli and the K10 control have been deposited on Jun. 9, 1989 with American Type Culture Collection according to the requirements of the Budapest Convention and are also readily available from the Coli Genetic Stock Center, New Haven, Connecticut. In such instances, the bacteria would perform this mutation or transposition in vivo and thereby prepare the altered protein.

In a further embodiment of the present invention contemplating in vitro activity, proteins of variant structure may be prepared by isolating a gene from an expression vector based on a particular target protein, incubating the gene with a protein structure modifying agent for a period of time sufficient for alteration of the gene to take place, recovering and separating the products of such incubation, followed by introducing one of such products into an expression vector which accumulates increased levels of a protein structure modifying agent thereby further increasing the modification of the target gee, and using such vector to express a protein of corresponding variant structure.

The protein structure modifying agent may be a reducing sugar, and more particularly, a reducing sugar selected from the group consisting of glucose, glucose 6-phosphate and the reaction product of glucose 6-phosphate and an amino acid.

The protein structure modifying agents are generally reducing sugars-as indicated earlier, but may include other materials comprising intermediate reaction products. In this connection, the preferred reaction product between glucose 6-phosphate and an amino acid, comprises the intermediate reaction product of glucose 6-phosphate and lysine.

The development of the present invention is a direct outgrowth of the original phenomenon observed by one of the inventors herein with respect to the reactivity between glucose and protein material. Clearly, it is this reactivity and the formation of the Amadori product that forms the cornerstone of the present invention, inasmuch as it is this glycosylation of proteins and/or nuclear material that causes genetic rearrangement which is the cornerstone of the present invention.

The present invention offers the possibility of preparing without chemical synthesis various mutant proteins which may permit the corresponding expression of mature proteins in various altered structures. Likewise, genes of known factors such as cachectin, Interleukin 1, and the like, may be incubated with the protein structure modifying agent, and if reacted therewith, may result in the expression of a mutant protein having certain of the properties or anti-properties of the factor.

The present invention also offers a wide variety of possibilities coupled with simplicity of practice.

Accordingly, it is a principal object of the present invention to provide a method for synthesizing proteins of altered structure without resort to standard techniques of chemical synthesis or genetic engineering.

It is a further object of the present invention to provide a method as aforesaid that relies upon the mutation of genetic materials to effect this synthesis.

It is a still further object of the present invention to provide a method as aforesaid which relies upon the reaction between protein coding material and materials that operate like reducing sugars.

It is a still further object of the present invention to provide a method for testing and discovering new agents capable of participating in protein structure modification, by use of bacteria specifically altered to be deficient in enzymes encouraging reducing sugar accumulation.

Other objects and advantages will be apparent to those skilled in the art from a review of the detailed description which proceeds with reference to the following illustrative drawings.

BRIEF DESCRIPTION OF THE DRAWINGS

FIG. 1 is a graph depicting the incorporation of [$^3$H]lysine into TCA precipitable material as a function of G-6-P concentration. $E.$ $coli$ DNA (1.3 mg/ml) was incubated with different concentrations of G-6-P (0.5M, ⚫; 0.25M,▬; 0.125M,♦; 0.05M,▲) in the presence of 20 $\mu$Ci/ml [$^3$H]lysine (97 Ci/mmole). Aliquots were taken at various time intervals for TCA precipitation (see Materials and Methods). The amount of nonspecific [$^3$H]lysine association in the control sample ($<10\%$ of the activity found in the 0.5M G-6-P sample on day 13) was subtracted from each value. The amount of incorporation is expressed as $\mu$ moles [$^3$H]lysine bound per $\mu$ mole DNA bases using the conversion of 325 $\mu$g DNA = $\mu$mole DNA bases.

FIG. 2A is a graph depicting the formation of reactive intermediates in the absence of $E.$ $coli$ DNA. 1 ml of 1M G-6-P and 20 $\mu$Ci [$^3$H]lysine (97 Ci/mmole) were incubated together. After a 4-day incubation a solution of $E.$ $coli$ DNA (825 $\mu$g/ml) was added. At the indicated times, samples were removed for TCA precipitation. The radioactivity incorporated into a control sample of Hepes buffer and [$^3$H]lysine was subtracted from each value. The amount of incorporation is expressed as $\mu$ moles [$^3$H]lysine bound per $\mu$ mole of DNA bases.

FIG. 2B is a graph depicting the accumulation of reactive intermediates as a function of time. 1M G-6-P and [$^3$H]lysine (20 $\mu$Ci/ml. 97 Ci/mmole) were incubated together. An aliquot was removed on days 0–6, to which an equal volume of $E.$ $coli$ DNA (330 $\mu$g/ml) was added. Following an additional 60 min. incubation, the samples were TCA precipitated.

DETAILED DESCRIPTION

Figure 3:
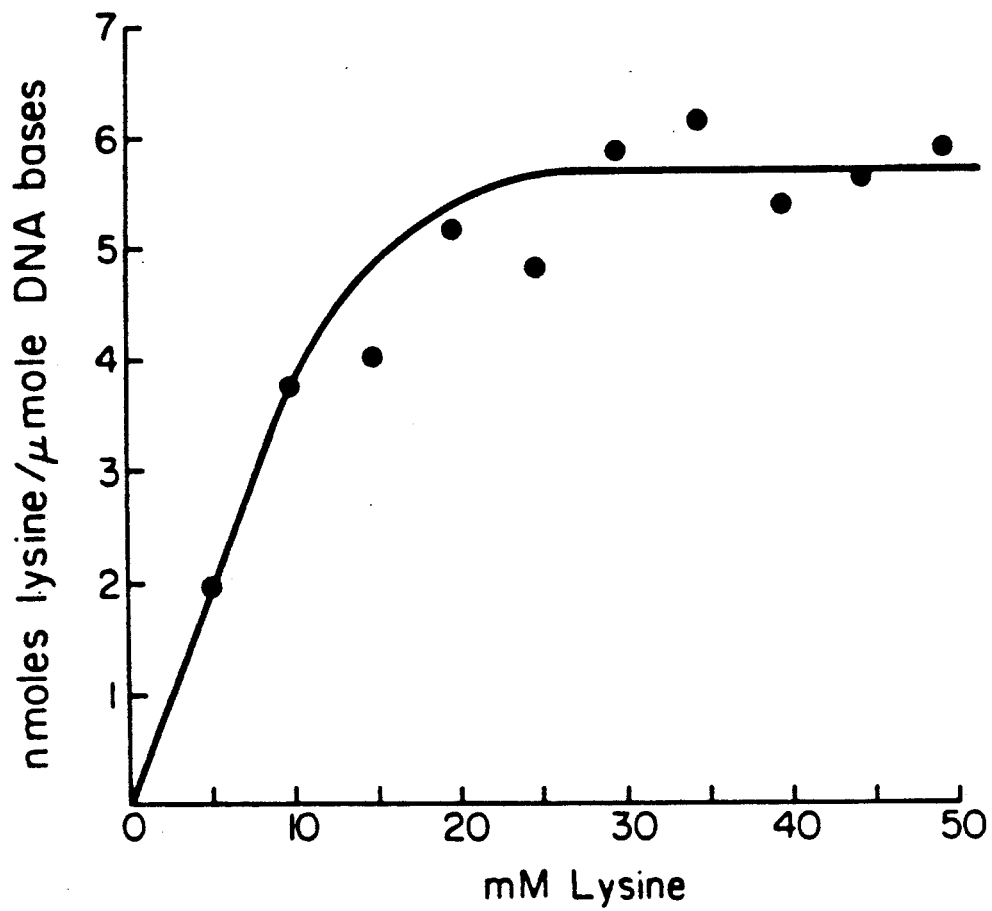
FIG. 3 is a graph depicting the saturable formation of G-6-P-lysine reactive intermediates. 1M G-6-P, 20 $\mu$Ci [$^3$H]lysine (97 Ci/mmole) and varying concentrations of unlabeled lysine were incubated together. Following a 4-day incubation period, $E.$ $coli$ DNA (1.3 mg/ml) was added and the incubation continued for 60 min. Samples were TCA precipitated. Presence of G-6-P-lysine-DNA complexes are expressed as nmoles lysine bound per $\mu$ mole DNA bases.

The present invention relates to the modification of cellular genetic material by reaction with protein structure modifying agents, such as reducing sugars, to cause the alteration in such genetic material. More specifically, genetic material such as DNA is modified by reducing sugars and/or reactive intermediates that may be formed by reducing sugars and amino acids to alter the genetic material directly or to prompt the movement of genetic insertion elements which can cause point, insertion and deletion mutants of the genetic material.

The present invention is predicated upon the discovery that genetic material like protein material undergoes a reaction with reducing sugars which corresponds to nonenzymatic glycosylation. The result of this reaction is the random modification of the genetic material and in some instances, the development of a broad variety of genetic mutants. This activity was first noted when, as stated earlier, it was observed that in DNA where nnenzymatic glycosylation had taken place, the ability of the DNA to undergo transfection or transformation had diminished. This loss in the ability of the genetic material to so respond to its environment prompted the consideration that some damage or other attenuation of the DNA was taking place. The investigations presented herein indicated that the reaction between the genetic material and the reducing sugars can result in significant mutations which can substantially change the structure and corresponding properties and abilities of the initial genetic material.

Accordingly, the present invention in its various aspects is predicated upon the fact that this reaction between the reducing sugars and the genetic material can be applied to the development of desired cellular alterations, by the promotion of such mutations and the subsequent screening for clones having the desired properties. In such instance, these clones may themselves be utilized. In a further embodiment, clones possessing certain genetic alterations or mutations may be introduced into a second cellular colony to cause the in vivo alteration of the genetic structure of the second colony to develop in turn, clones having desired properties.

Accordingly, and in a first aspect of the invention, proteins of altered structure may be prepared from a target genetic material by incubating a protein structure modifying agent with the target genetic material under conditions conducive for causing mutation, thereafter recovering the reacted target genetic material and introducing that material into a particular cellular strain to promote the occurrence of mutations. Thereafter, the resulting mass may be screened for genetic clones of the cellular strain that provide a protein material having an altered structure with certain desired properties. Such clones may then be recovered for later use.

An in vivo modification of the above method contemplates the introduction of a particular gene into a cell which has increased intracellular levels of the reducing sugar, such as the DF40 and DF2000 strains referred to earlier and illustrated later on herein. In such instance, the bacteria performs the mutation or transposition in vivo and the altered protein is thereby prepared.

A further in vitro variant of the present invention constitutes the isolation of a gene from an expression vector based on a particular target protein following by the incubation of that gene with a protein structure modifying agent for purposes of mutation thereof followed by the recovery, separation and thereafter introduction of the products of such incubation into an expression vector which itself accumulates increased levels of the protein structure modifying agent so as to further enhance and increase the modification of the target gene. Such vector might then be utilized to express a protein of corresponding variant structure.

A still further modification of the present invention contemplates the preparation of a protein of altered structure by the incubation of a nontarget gene with the protein structure modifying agent followed by the introduction of the nontarget gene so modified into the target cell to cause the nucleotide rearrangement and mutation of the latter.

As mentioned earlier, suitable protein structure modifying agents comprise the reducing sugars and more particularly, reducing sugars selected from the group consisting of glucose, glucose 6-phosphate and the reaction product of glucose 6-phosphate and an amino acid. A particular reaction product contemplated herein comprises the intermediate reaction product of glucose 6-phosphate and lysine. Naturally, other materials having similar activity are contemplated herein, and the invention is not limited to the foregoing recitation in operability or scope.

Where utilized in the present Specification, the term "genetic material" is intended to cover the DNA and RNA. Moreover, both plasmid DNA and phage DNA are contemplated and may be utilized herein.

The following Examples are presented to illustrate the activity of the reducing sugars as promoters of mutation of genetic material.

EXAMPLE I

In the present study a model reaction of glucose 6-phosphate (G-6-P) with the amino groups of lysine and putrescine was investigated to form reactive intermediates which are capable of rapidly reacting with DNA to form stable covalent adducts. The formation of these reactive intermediates occurs in a concentration- and time-dependent manner and once formed are insensitive to the addition of aminoguanidine and to reduction by sodium borohydride.

E. coli and Plasmid DNA Isolation

Cultures of E. coli strain K38 were grown in 1 l of LB broth (Gibco, Madison, Wis.). After overnight growth, the bacteria were harvested by centrifugation and resuspended in 1.7 ml TES (50 mM Tris-HCl buffer pH 8.0, 25% sucrose with 1 mM EDTA), and transferred to a Beckman Quick Seal tube (Beckman Co., Palo Alto, Calif.). The following materials were added to each tube: 0.4 ml of 10 mg/ml lysozyme (Sigma Chemicals, St. Louis, Mo.). 10 μl of 20 mg/ml proteinase K (Bethesda Research Laboratories, Bethesda, Md.), 0.5 ml of 0.4M EDTA pH 8.0, and 0.2 ml 10% Sarkosyl to give a final volume of 2.8 ml. The lysate was incubated at 65° C. in a shaking waterbath for 3 h, after which an additional 10 μl of proteinase K was added, and the incubation continued for an additional hour.

Following the incubations, 33 ml of 126 g CsCl/100 ml TESP (50 mM Tris-HCl buffer pH 8.0, 5 mm EDTA, 50 mM NaCl and 5 mg/ml phenylmethylsulfonylfluoride), was layered under the lysate. The tubes were filled with mineral oil and sealed. Ultracentrifugation was carried out in a Beckman Vti50 rotor at 113,000 ×g, 20° C. After 19 h of centrifugation, the tubes were punctured and the contents of the tube were allowed to drip out by unit gravity. The DNA was dialyzed twice against a 1000-fold excess of 10 mM Tris-HCl buffer pH 8.0, 1 mM EDTA followed by dialysis against 100 mM Hepes buffer pH 8.0, 1 mM EDTA at 4° C. The concentration of DNA was determined by measuring the absorbance at 260 nm.

E. coli strain K38 were transformed with pBR322 and the plasmid isolated as described previously (Maniatis et al., 1982).

Incubation and Assay Conditions

All incubation solutions were filter sterilized or autoclaved and maintained sealed in a 37° C. dry incubator. In experiments monitoring the time-dependent incorporation of [$^3$H]lysine into acid-precipitable material, a solution of DNA was added to an equal volume of 1, 0.5, 0.25, or 0.1M glucose 6-phosphate (G-6-P) (Calbiochem, San Diego, Calif.) dissolved in 100 mM Hepes buffer pH 8.0, 1 mM EDTA, containing 20 μCi/ml of [$^3$H]lysine (spec. act. 97 Ci/mmole, New England Nuclear, Boston, Mass.). Under these conditions the pH of the solution decreased slightly during the incubation period.

To measure the presence of reactive intermediates 1M G-6-P was dissolved in 100 mM Hepes buffer, pH 8.0, 1 mM EDTA and preincubated with 20 μCi/ml of either [$^3$]lysine (97 Ci/mmole) or [$^3$H]putrescine (28.8 Ci/mmole) (New England Nuclear) for 4 days. Following the initial incubation period, an equal volume of solution of DNA was added to the preincubated mixture and incubated for an additional 60 min. Control samples contained no G-6-P in the preincubation mixture, and the values for nonspecific incorporation were subtracted form the experimental values. This background represented less than 10% of the experimental points. The experiments were done at least twice and the data shown are representative of the results.

Inhibition studies were carried out in the presence of either aminoguanidine hydrochloride or sodium borohydride. Aminoguanidine hydrochloride (1M) which inhibits the formation of protein crosslinks (Brownlee et al., 1986) was either preincubated for 4 days with 1M G-6-P and 20 μCi[$^3$H]lysine (97 Ci/mmole) or added following the 4-day preincubation period for 60 min. prior to the addition of the DNA solution. An equal volume of the DNA solution was then added followed by an additional 60-min. incubation. NaBH$_4$ (2 mg/ml), which reduces the Amadori product of G-6-P and lysine, was added to samples containing a 4-day incubation of 0.5M G-6-P, 20 μCi [$^3$H]lysine (97 Ci/mmole) and DNA; NaBH$_4$ (2 mg/ml) was also added to 4-day preincubated samples containing 1M G-6-P and 20 μCi of [$^3$H]lysine (97 Ci/mmole) for 15 min. prior to the addition of DNA and a 60-min. incubation.

Trichloroacetic Acid (TCA) Precipitation

Duplicate samples were TCA precipitated in 16 vol. of ice-cold 10% TA and allowed to sit on ice for 30 min.

The samples were then filtered through prewetted Whatman GF/C filter discs in an Amicon filtration unit. The discs were washed twice with 5 ml of 10% cold TCA and 3 times with an excess of 5% cold TCA. The final two washes were done with 100% cold ethanol. The duplicate filters were counted in a Beckman beta scintillation counter with 10 ml of scintillation fluid (Hydrofluor, Natonal Diagnostics, Highland Park, N.J.). The data points shown represent the average of 2 filters.

RESULTS

Preliminary experiments using calf thymus DNA revealed a rapid uptake of radiolabeled lysine into an acid-precipitable form. This reaction occurred in both the presence and absence of added G-6-P. Presumably this reflected the reaction of the lysine with free aldehydes present in the DNA as a result of depurination of bases since reduction of the calf thymus DNA with NaBH$_4$ reduced the amount incorporated (data not shown). To avoid this problem we utilized freshly prepared DNA from stationary phase E. coli.

The incorporation of [$^3$H]lysine into acid-precipitable E. coli DNA with time in the presence of increasing amounts of G-6-P is shown in FIG. 1. Following a 2-day lag period, incorporation of [$^3$H]lysine onto DNA increased with the concentration of G-6-P as monitored by TCA-precipitable radioactivity.

Under these conditions the incorporation of lysine without added G-6-P was not significant (<10%). However, to eliminate further the possibility of [$^3$H]lysine incorporation due to depurination during the incubation period, the formation of reactive intermediates was allowed to occur in the absence of DNA. After a 4-day preincubation o G-6-P (1M) and [$^3$H]lysine (20 μCi; spec. act. 97 Ci/mmole), E. coli DNA was added to the incubation mixture and aliquots were removed at the indicated times and TCA precipitated. FIG. 2A shows the time-dependent reaction of E. coli DNA with a 4-day preincubation mixture of [$^3$H]lysine and G-6-P. Within 1 h after addition, all of the reactive intermediates present have reacted with the added DNA. This demonstrates the ability of the preformed intermediates to react rapidly with the DNA to form acid-stable complexes. Addition of DNA to G-6-P or [$^3$H]lysine which had been preincubated alone for 4 days and then added to the missing components did not lead to incorporation of radiolabel (Table 1).

This type of assay allows the detection and measurement of reactive intermediates formed by G-6-P and [$^3$H]lysine which can crosslink lysine to DNA. As shown in FIG. 2B, the preincubation of G-6-P and [$^3$H]lysine results in the time-dependent accumulation of reactive intermediates. In this experiment, aliquots of the preincubation mixture were assayed at the indicated times for the presence of reactive intermediates which can crosslink lysine to the E. coli DNA. After a 1-day lag period there is a logarithmic accumulation of the reactive intermediate(s). Although the chemical nature of the reactive intermediate(s) formed between G-6-P and lysine is unknown, it does appear to require the presence of an amino group on the polynucleotide for maximum stable adduct formation with the DNA. Addition of poly(dA) to a 4-day preincubation mixture of G-6-P and [$^3$H]lysine led to significant acid-precipitable material whereas the addition of poly(dT) did not (Table 2). In addition, polydinucleotides d(A-T) and d(C-G) as well as pBR322 (DNA could react with the reactive intermediate(s) to form stable adducts (Table 2).

TABLE 1

THE PRESENCE OF GLUCOSE-6-PHOSPHATE AND LYSINE IN THE PREINCUBATION MIXTURE IS NECESSARY FOR THE FORMATION OF REACTIVE INTERMEDIATES

| 4-day preincubation at 37° C.[a] | 60-min incubation at 37° C.[b] | (μ moles [$^3$H] lysine per μ moles DNA bases) × 10$^9$ |
|---|---|---|
| G-6-P | +(DNA + [$^3$]lysine) | 3.6 |
| [$^3$H]lysine | +(G-6-P + DNA) | 2.2 |
| DNA | +(G-6-P + [$^3$H]lysine) | 2.8 |
| G-6-P + [$^3$H]lysine | +(DNA) | 100.0 |

[a] A 1-ml solution of 1M G-6-P, 20μ Ci of [$^3$H]lysine (97 Ci/mmole) in 0.1M Hepes buffer, E. coli DNA (643 μg/ml) or 1M G-6-P and 20μ Ci of [$^3$H]lysine were incubated at 37° C. for 4 days.
[b] 1 ml of E. coli DNA (643 μg/ml) and 20μ Ci of [$^3$H]lysine (97 Ci/mmole), 643 g of E. coli DNA in 1M G-6-P, 20μ Ci [$^3$H]lysine (97 Ci/mmole) in 1M G-6-P, or 643 μg of E. coli DNA was added as indicated to the 4-days preincubation mixture for 60 min prior to TCA precipitation.

In the model reactions described above, [$^3$H]lysine was used at a very high specific activity (97 Ci/mmole) and G-6-P at very high concentrations. The full extent of possible G-6-P-lysine complex formation may have been limited by the amount of lysine present. FIG. 3 demonstrates the maximum amount of lysine incorporated onto E. coli DNA following preincubation of 1M G-6-P ;with lysine at decreasing specific activities. Under these conditions the maximal amount of lysine incorporated onto DNA was approximately 6 nmoles/μmole of DNA which occurred at a lysine concentration of approximately 25 mM. Further additions of unlabeled lysine did not increase the amount of crosslinks formed with the DNA. This saturable level of reactive intermediate complex formation supports the interaction of the G-6-P and lysine reaction with DNA. It is possible that more reactive intermediates are formed between lysine and G-6-P, but they may be reacting with free lysine during the preincubation time.

Figure 4:
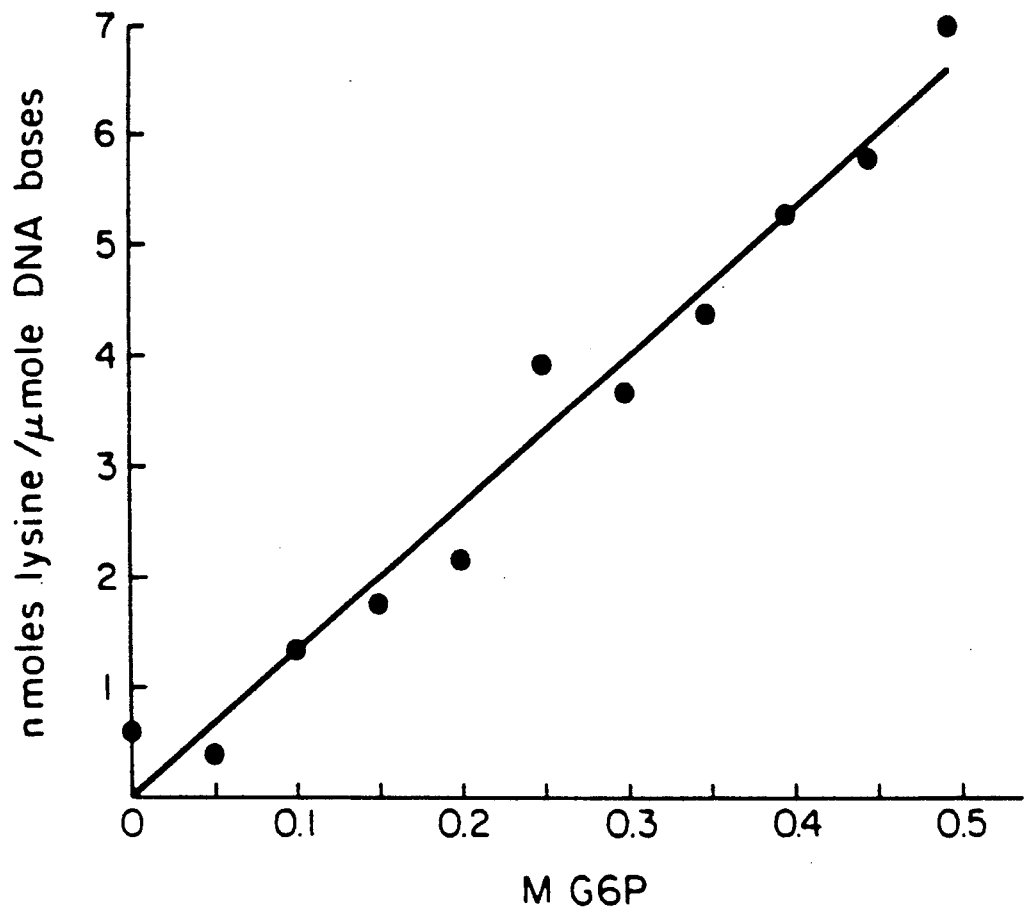
FIG. 4 is a graph depicting the formation of reactive intermediates as a function of G-6-P in the presence of 25 mM unlabeled lysine. The incubation mixture consisted of 20 $\mu$Ci of [$^3$H]lysine (97 Ci/mmole) in 25 mM unlabeled lysine with varying concentrations of G-6-P. After 4 days of incubation, $E.$ $coli$ DNA (643 $\mu$g/ml) was added, followed by an additional 60-min incubation period after which samples were TCA precipitated. The presence of crosslinks is expressed as nmoles lysine bound per $\mu$ mole DNA bases. The line drawn represents the regression equation: $y = 13.02 \times 10^{-3}(X) + 3.75 \times 10^{-5}$ with a correlation coefficient of 0.985, and was derived from the experimental data shown.
Figure 5:
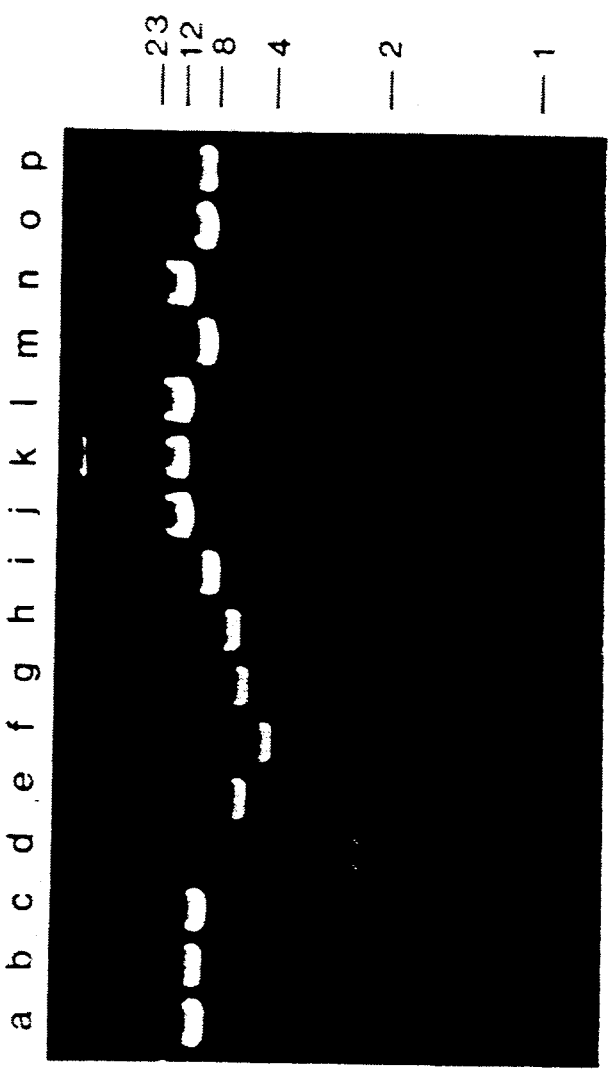
FIG. 5 is a photograph of a gel representing restriction analysis of mutated plasmid DNA from $E.$ $coli$ strains K10, DF40, and DF2000. Plasmid DNA was prepared on a small scale from 14 cultures of Amp$^R$-/Lac$^-$ colonies, digested with Xba 1, and separated on a 1% agarose gel containing ethidium bromide at 1.0 $\mu$g/ml. Size standards are given as kilobase pairs. Lanes: a and p, pAM006; b-e, K10; f-i, DF40; j-o, DF2000.

To further substantiate this G-6-P lysine complex formation, the reverse experiment was done. In this case, a fixed concentration of lysine was added to increasing amounts of G-6-P. The preincubation of 25 mM lysine with increasing concentrations of G-6-P for 4 days prior to the addition of E. coli DNA showed a linear increase of lysine incorporated onto the DNA with increasing G-6-P concentrations (FIG. 4).

The formation of a reactive intermediate between lysine and G-6-P implies that other molecules bearing free amino groups may also form a reactive intermediate(s). To test this hypothesis, the number of crosslinks formed between G-6-P and [$^3$H]putrescine instead of [$^3$H]lysine was measured. Under similar conditions, [$^3$H]putrescine was a more potent mediator of crosslink formation than [$^3$H]lysine (Table 2).

TABLE 2

INCORPORATION OF [$^3$H]LYSINE OR [$^3$H]PUTRESCINE ONTO DNA

| DNA | (μ moles [$^3$H]lysine per μ moles DNA bases) × 10$^7$ | μ moles[$^3$H] putrescine per μ moles DNA bases) × 10$^6$ |
|---|---|---|
| E. coli | 1.0 | 0.8 |
| pBR322 | 9.6 | 7.5 |
| poly(d(C-G)) | 3.0 | 2.5 |
| poly(d(A-T) | 1.8 | 1.6 |
| poly(dA) | 4.8 | 5.3 |

TABLE 2-continued

INCORPORATION OF [$^3$H]LYSINE OR [$^3$H]PUTRESCINE ONTO DNA

| | | |
|---|---|---|
| poly(dT) | 0.19 | 0.05 |

Formation of the reactive intermediate(s) between G-6P and lysine can be inhibited if 1M aminoguanidine is added to the mixture at the beginning of the incubation (Table 3). However, the addition of aminoguanidine (1m) to the incubation mixture for an hour at 37° C. to the reactive intermediate(s) present after a 4-day incubation of G-6-P and lysine had no significant effect on the subsequent formation of stable adducts with DNA. The addition of 2 mg/ml of sodium borohydrate to the incubation mixture before or after the formation of these intermediates also had little effect on stable adduct formation with DNA (Table 3).

TABLE 3

INHIBITION STUDIES

| | ($\mu$ moles [$^3$H]lysine per $\mu$ moles DNA bases) × 10$^7$ | | |
|---|---|---|---|
| | Day 0 | Day 4 | None |
| (1) Aminoguanidine 1M aminoguanidine added to the pre-incubation mixture | 0.06 | 1.3 | 1.3 |

| | ($\mu$ moles [$^3$H]lysine per $\mu$ moles DNA bases) × 10$^7$ | |
|---|---|---|
| | −NaBH$_4$ | +NaBH$_4$ |
| (2) Sodium borohydride | | |
| Complete incubation mixture | 1.8 | 1.5 |
| Preincubation mixture | 0.81 | 0.87 |

DISCUSSION

Previous studies have shown that glucose 6-phosphate (G-6-P) can form covalent adducts with DNA which interferes with biological activity (Bucala et al., 1984, 1985). The above experiments and data demonstrate that G-6-P can react with primary amino groups of lysine and putrescine to form with time (days) a stable reactive intermediate which can react rapidly (minutes) with DNA. In both reactions thymidine residues were poor substrates for DNA adduct formation, pointing to the importance of the amino groups on the bases.

However, in sharp contrast to the reaction of G-6-P with DNA which was much faster with single-stranded DNA than double-stranded DNA, the G-6-P-lysine intermediate reacted equally well with single-stranded and double-stranded DNA (Table 2). A possible explanation for this is that during the preincubation period the G-6-P and lysine form a cyclic intermediate that can intercalate with double-stranded DNA and associate with the bases of single-stranded DNA, to allow the formation of covalent adducts with amino-containing bases of the DNA. The interaction of G-6-P with DNA, on the other hand, appears to require the availability of a non-hydrogen bonded amino group on the base as an initial step in the reaction. It should also be noted that the reactivity of the G-6-P lysine intermediate is greater with plasmid pBR322 DNA than with E. coli DNA. Similar increased rates have also been observed with other plasmid DNA constructs (unpublished observations). Whether this represents a predilection of the reactive intermediate(s) for plasmid DNA or small DNA in general is now being investigated.

The chemical nature of the G-6-P-lysine intermediate is not known. At present the structure of only one rearrangement product of glucose or G-6-P with proteins is known, 2-(2-furoyl)-4(5)-(2-furanyl)-1H-imidazole (FFI). This product presumably arises by the condensation of two Amadori products to form an imidazole with subsequent ring closure and dehydrations to form the two furan rings (Pongor et al., 1984). The inability of aminoguanidine or NaBH$_4$ to prevent the G-6-P-lysine intermediate from reacting with DNA suggests that the intermediate lacks a carbonyl moiety and has advanced beyond the Amadori product stage. Future studies will have to establish the identity of this intermediate.

Although unusually high concentrations of G-6-P were used in the early model studies for the formation of G-6-P lysine intermediates (FIG. 2A and B), it is apparent that the G-6-P-lysine intermediate can form at concentrations closer to that of physiological conditions (FIG. 1; see also Bucala et al., 1984, 1985). As in all of these nonenzymatic rearrangement reactions, accumulation of intermediates over time will eventually produce significant amounts of product. In fact, the slow time-dependent formation of a protein-bound equivalent of the G-6-P-lysine intermediate may explain the accumulation with age of proteins bound covalently to DNA (Bojanovic et al., 1970). It also implies that this reaction could occur in the nucleus in a specific manner, with sugars entering attached to nuclear proteins. Since Schiff base and Amadori products are found ubiquitously on all proteins, a DNA binding protein made in the cytoplasm could carry the bound sugar into the nucleus and hold in propinquity the attached sugar until the subsequent rearrangements occur, thus facilitating the reaction with DNA.

EXAMPLE II

In the following experiment the in vivo reaction dynamics of the reducing sugar glucose 6-phosphate were examined. In particular two strains of E. coli defective for the enzyme phosphoglucose isomerase or phosphoglucose isomerase and glucose 6-phosphate dehydrogenase, respectively, and thereby possessing elevated levels of glucose 6-phosphate, were used as models. To facilitate the measurement of the rate of mutation, a plasmid-carried marker gene was introduced into both model strains as well as a control strain of E. coli. The details of the experiments are presented below.

MATERIALS AND METHODS

Bacterial Strains

The following K-12 E. coli strains were used: (i) K10 HFr [tonA22, omp F626, relA1, pit-10, spoT1, T2$^R$; (Coli Genetic Stock Center, New Haven, Conn.) CGSC 4234], (ii) DF40 HFr [ton A22, omp F626, relA1, pit-10, spo T1, T2$^R$, pgi-2, CGSC 4861], (iii) DF2000 HFr [ton A22, rel A1, T2$^R$, pgi-2, zwfA2; CGSC 4863], (iv) SB4288 F$^-$[($\Delta$lac-proB, recA, thi-l, relA, mal-24, spcl2, supE-50, DE5], Strains K10, DF40, and DF2000 were transformed with pAM006 by standard calcium chloride treatment (Maniatis, et al. Supra.)

Plasmids

The plasmids, pAM006 and pKM005, were a gift from P. Green (Rockefeller University, New York) and M. Inouye (Rutgers University, New Jersey), pKM005 carries the gene conferring ampicillin resistance (Amp$^R$) and inactive, promoterless lacZ and lacY genes (Masui, et als., (1983) Experimental Manipulation of Gene Expression: Academic Press, NY; pp. 15-32) pAM006 was derived by the insertion of the ompA promoter upstream of lacZ to activate lacZ and lacY transcription (Green, P. J. (1985) Ph.D. Thesis, SUNY at Stony Brook, Stony Brook, N.Y.).

Media and Buffers

M63 minimal medium was prepared as described by Miller (Miller, J. H. (ed.) (1962) Experiments in Molecular Genetics, Cold Spring Harbor Lab., Cold Spring Harbor, N.Y.) with the addition of 2% (wt/vol) glucose and gluconate in the mass ratios indicated or of 2% (wt/vol) gluconate, supplemented with ampicillin at 100 μg/ml. MacConkey agar (Difco) plates and LB broth (GIBCO) were prepared as directed by the manufacturers and supplemented with ampicillin at 100 g/ml.

Growth Conditions

The transformed strains were grown in 500 ml of M63 medium containing gluconate alone or glucose and gluconate in a 9:1 mass ratio for 24 hr in a 37° C. shaking water bath. Cultures were regularly checked for revertants in the mutant strains. Attempts to extend the experimental growth period beyond 24 hr led to an increased occurrence of revertants and prevented analysis. Under these conditions the growth rate of DF40 and DF2000 strains was slower by factors of 2 and 6, respectively, than the K10 control strain. The growth of the K10 strain did not change significantly when grown either in glucose/gluconate or gluconate minimal medium. Following growth, a sample was removed for G-6-P content analysis (see below): the remaining culture was harvested, and plasmid DNA was isolated as described by Maniatis et al. (9).

Detection of Plasmid Mutations

The purified plasmid from each strain was transformed separately into competent SB4288 cells that had been frozen as described by Hanahan (Hanahan, D. (1985) in DNA Cloning, A Practical Approach, ed. Glover, D. M.; IRL Press, Washington, D.C.; 1: 109-135) and plated out on MacConkey lactose indicator plates. Transformants from pAM006 and pKM005 were used as positive and negative controls, respectively. Those colonies exhibiting Amp$^R$ but unable to ferment lactose were isolated, rescreened, and grown in LB broth overnight. The plasmid from each mutant colony was isolated on a small scale (Maniatis, et al. Supra.), linearized with Xba I, treated with RNase A (50 μg/ml), and electrophoresed on a 1.0% agarose gel containing ethidium bromide.

Glucose 6-Phosphate Assay

Each culture was diluted to give an OD$_{550}$ reading of 1.0 ($10^8$ cells per ml). Fifty milliliters of the diluted culture was centrifuged at 3000 ×g for 30 min at 4° C. The pelleted culture was extracted with 5 ml of 6M perchloric acid then 2 ml of 3M perchloric acid. The pH of the combined supernatants was adjusted to 3.5 then assayed in triplicate. G-6-P was measured by the coupled reaction of glucose-6-phosphate dehydrogenase to NADPH production (Lang, G., et al. (1964) Methods of Enzymatic Analysis, ed. Bergmeyer, H. U.; Academic Press, Inc, N.Y. 3: 238-1242). Increase in absorbance was monitored at 340 nm.

RESULTS

All three strains (K10, DF40, and DF2000) are capable of utilizing gluconate as a sole carbon source (See Fraenkel, (1968) J. BACTERIOL. 95: 1261-1266; Fraenkel, et al., (1966) J. BACTERIOL. 93: 1561-1568). When grown in gluconate minimal medium, neither of the mutant strains (DF40 and DF2000) accumulated significant levels of G-6-P; however, the presence of glucose in the medium led to the accumulation of G-6-P. Table 4 shows the concentrations of intracellular G-6-P found in each strain when grown for a 24-hr period in medium containing the glucose/gluconate mass ratios 9:1, 7:3, and 1:1. The 9:1 ratio of glucose to gluconate was chosen for the calculation of mutation rates since the concentration of intracellular G-6-P was highest at this ratio. Under these conditions the DF40 strain accumulated approximately 20 times more G-6-P than the control strain K10, whereas DF2000 accumulated approximately 30 times more. When the concentration of G-6-P was analyzed in the K10, DF40, and DF2000 strains after growth on gluconate minimal medium, no significant accumulation of G-6-P was detected.

TABLE 4

| | G-6-P LEVELS FOUND IN CELLS GROWN IN MINIMAL MEDIUM CONTAINING GLUCOSE/ GLUCONATE OR GLUCONATE ALONE | | | |
|---|---|---|---|---|
| | G-6-P, per 5 × $10^9$ cells | | | |
| | | Glucose/ gluconate | | Gluconate alone |
| Strain | 9:1 mass ratio* | 7:3 mass ratio+ | 1:1 mass ratio+ | |
| K10 | 0.028 ± 0.005 | 0.0177 ± 0.0031 | 0.0183 ± 0.0029 | 0.030[1] |
| DF40 | 0.553 ± 0.072 | 0.3478 ± 0.0230 | 0.1636 ± 0.0593 | 0.005[2] |
| DF2000 | 0.864 ± 0.011 | 0.6319 ± 0.0374 | 0.3230 ± 0.0796 | 0.004[3] |

Overnight cultures of each strain grown either in gluconate or glucose/gluconate minimal medium were diluted to $10^8$ cells per ml. Diluted culture (50 ml) was extracted with perchloric acid then assayed for G-6-P content.
*The results are means of triplicate experiments ±SD.
+The results are means of duplicate experiments ± SD.
[1] ±0.003
[2] ±0.002
[3] ±0.001

Plasmid DNA was isolated and purified from each strain following growth on minimal medium containing gluconate along or glucose/gluconate. The isolated plasmid DNA was used to transform the lactose utilization deficient (Lac−), *E. coli* strain SB4288. The transformants were selected for Amp$^R$ and screened of β-galactosidase production on MacConkey plates supplemented with ampicillin. Those colonies displaying an Amp$^R$/Lac− phenotype were isolated and rescreened. The relative number of mutants per $10^5$ transformants is given by the ratio of mutants found in the test strain (DF40 or DF2000) divided by the number of mutants found in the control strain (K10) (Table 5). The number of mutants increases proportionately in those strains that accumulated G-6-P. The relative number of mutants increased 7-fold with plasmid isolated from the DF40 strain and 13-fold with plasmid isolated from the DF2000 strain. This relationship is dependent on G-6-P since no increase is observed when the strains are grown in the absence of glucose.

To further characterize the mutations that had occurred as a result of elevated G-6-P levels, isolated plasmid DNA was analyzed from the AmpR/Lac− colonies. Table 6 summarizes the ratio of plasmid size changes per $10^5$ transformants observed in the mutated plasmids from each strain. The background mutations in the K10 control strain and the plasmid mutations that originated from the DF40 strain show a predominance in plasmid size decrease. The mutations found in plasmid DNA isolated from the DF2000 strain appear to be distributed mainly between minor size changes and plasmid size increase. The cause or causes for variations in plasmid size ratios are not known at this time. FIG. 6 shows a representative sample of linearized, mutated plasmids isolated from each of the strains.

TABLE 5

RELATIVE MUTATION RATES OF CELLS GROWN IN GLUCONATE ALONE OR GLUCOSE/GLUCONATE

| Strain | Relative lac− mutants per $10^5$ transformants | |
|---|---|---|
| | Glucose/gluconate* | Gluconate alone+ |
| K10 | 0.67 ± 0.47 | 0.5 ± 0.5 |
| DF40 | 4.84 ± 0.65° | 1.0 ± 1.0 |
| DF2000 | 8.71 ± 1.24° | 1.5 ± 0.5 |

Plasmid DNA (50 ng) isolated from cultures grown in gluconate or glucose/gluconate minimal medium was used to transform SB4288 competent cells. Colonies that were Amp$^R$ but had a Lac− phenotype were scored as mutants. Relative mutagenesis was determined by the ratio of mutants found in the mutant strains (DF40 or DF2000)/control (K10 strain).
*The results are means of triplicate experiments ± SD.
+The results are means of duplicate experiments ± SD.
°The difference in mutation rate between K10 and the mutant strains DF40 and DF2000 is statistically significant (P < 0.0001).

TABLE 6

PLASMID SIZE CHANGES

| Size change | Fraction of total plasmids with size changes | | | | | |
|---|---|---|---|---|---|---|
| | K10 | | DF40 | | DF2000 | |
| >1Kb increase | 3/12 | (25.0%) | 24/78 | (30.8%) | 75/153 | (49.0%) |
| >Kb decrease | 8/12 | (66.7%) | 54/78 | (69.2%) | 27/153 | (17.6%) |
| <1Kb change in either direction | 1/12 | (8.3%) | 0/78 | (0.0%) | 51/153 | (33.4%) |

Plasmid DNA from phenotypic Amp$^R$/Lac− colonies was isolated and linearized with XbaI. Samples were treated with RNase A and visualized on a 1.0% agarose gel containing ethidium bromide at 1.0 μg/ml. Twelve plasmids with size changes were isolated from $10^5$ K10 transformants, 78 plasmids with size changes were isolated from $10^5$ DF40 transformants, and 153 plasmids with size changes were isolated from $10^5$ DF2000 transformants. Plasmids were grouped as indicated, and the percentage of the total plasmids isolated from each transformant strain is in parenthesis.

DISCUSSION

The above shows that raising the intracellular levels of G-6-P is associated with an increased rate of mutation of plasmid DNA. A comparison of G-6-P levels (Table 4) and plasmid mutation rates (Table 5) suggests a correlation between the intracellular G-6-P concentration and plasmid mutation rate. The control strain K10 shows minimal G-6-P accumulation over a 24-hr growth period in glucose/gluconate minimal medium, whereas the DF40 phosphoglucose isomerase-deficient) and DF2000 phosphoglucose isomerase- and glucose-6-phosphate dehydrogenase-deficient) strains accumulate 20- and 30-fold more G-6-P respectively. The relative mutation rates for each of the strains increase with intracellular G-6-P concentrations. A 13-fold increase in mutation rate occurs in the plasmid present in the DF2000 strain, whereas a 7-fold increase over background is observed in the DF40 strain. It seems likely that the increase in mutations is related to the higher intracellular G-6-P concentrations since growth of the mutant bacterial strains in gluconate minimal medium does not increase the intracellular G-6-P levels or the plasmid mutation frequency.

The *E. coli* strains K10, DF40, and DF2000 are not repair-deficient strains, suggesting that any mutations observed were those that were not repaired or were repaired incorrectly. Studies on the mutagenic effects of incubation in vitro of plasmid DNA with G-6-P indicate that some of the mutations that occurred were due to the attempts of the *E. coli* host to repair the plasmid DNA. When glycosylated plasmid DNA was transformed into a uvrC−*E. coli* strain, no plasmid mutations were found. This is in strong contrast to the variety of insertions, deletions, and point mutations that were observed when the glycosylated plasmid was transformed into a wild-type strain (Bucala, et al. (1984) Supra.). We have preliminary results that indicate that there is no significant induction of RecA when the bacteria are grown in gluconate minimal medium in the presence or absence of glucose (data not shown).

In the above experiments, the number of mutations observed may be an underestimate of the actual number that have occurred. Some of the mutations that would have been overlooked in this assay include: mutations affecting the *E. coli* genome, mutations affecting Amp$^R$, plasmid replication, or more than one mutation in the lacZ and/or lacY genes, since a Lac− phenotype on MacConkey plates does not distinguish between plasmids with defective lactose permease or β-galactosidase genes or both.

The exact mechanism of the increased occurrence of the Lac− mutants observed in bacterial strains that accumulate G-6-P cannot be defined with certainty at the present. Two obvious hypotheses are that the elevated intracellular G-6-P activates a recombination/repair mechanism that promotes mutations in the plasmid or that the G-6-P is reacting with the plasmid DNA to induce mutations by analogy to those observed following in vitro incubations of G-6-P and DNA. This latter mechanism could occur by direct addition of the G-6-P to the DNA or following the formation of a reactive intermediate with proteins or polyamines that can rapidly react with DNA (Lee, A. T., et al, (1987) Supra.). Although either of these adducts can form readily under in vitro conditions, they have not been identified under in vivo conditions.

EXAMPLE III

In this example, certain types of mutations that were detailed in Example II have been examined for purposes of identification. Accordingly, a number of mutations which increased the size of the target plasmid were found to be due to the transposition of a transposable element ($\gamma\delta$) onto the plasmid. This transposable element was identified by Southern hydridizations and restriction digest analyses. Elevated levels of glucose 6-phosphate in the mutant E. coli DF40 and DF2000 not only induce plasmid mutations in a concentration dependent manner, but also increase the rate of transposition invivo, as well. Of the mutations found in plasmids from the DF2000 strain, approximately 50% were due to the transposition of the transposon $\gamma\delta$. Transposition of $\gamma\delta$ accounted for approximately 30% of the plasmid mutations found in the DF40 strain. Background mutations in plasmids from the K10 wild type strain showed only 0.08% mutations due to transposition of $\gamma\delta$. The mechanisms for the mutations and transposition observed in the plasmids have not yet been elucidated but in general, most mutagens do not induce transposon movement. It appears that DNA that has reacted with a protein modifying agent elicits the movement of transposable elements such as the transposon $\gamma\delta$, to result in a wide array of mutated genes. A possible use of glucose 6-phosphate as a mutagen would be to generate many mutations in a particular gene carried in an expression vector that would in turn express a mutated protein. The use of glucose 6-phosphate for in vivo mutagenesis would enable one to generate many different forms of a protein with little effort. The use of glucose 6-phosphate to induce mutations is a powerful and simple method of generating a variety of forms of the a protein with properties that are desired (e.g. greater activity or an antagonist).

EXAMPLE IV

Preliminary results have shown that there is a decrease n transformation capacity as well as an increase in plasmid mutation rates when the plasmid DNA is reacted with the glucose 6-phosphate-lysine intermediate prior to transformation into a bacterial host (DF2000) which accumulates an elevated level of G-6-P.

MATERIALS AND METHODS

A filter sterilized solution of 1M glucose 6-phosphate, 10 mM lysine, 100 mM HEPES buffer, 1 mM EDTA was incubated for 4 days at 37° C. Following the incubation period, aliquots of the solution was added to isolated plasmid DNA to give a final volume of 200 μl then incubated an additional 60 minutes at 37° C. Fifty nanograms of the reacted plasmid pAM006 DNA was used to transform competent DF2000 cells. The transformed cells were then grown overnight in a 37° C. shaking water bath, in minimal medium (M63) with the addition of 2% (wt/vol) glucose and gluconate in a 9:1 mass ratio, supplemented with 100 μg/ml ampicillin. The bacteria were harvested and plasmid DNA was isolated as previously described. Fifty nanograms of the purified plasmid were then used to transform competent SB4288 cells. The transformed cells were then grown on lactose indicator plates supplemented with ampicillin. Those colonies which were unable to ferment lactose but were ampicillin resistant were scored as mutants.

RESULTS

The addition of increasing concentrations of the reactive intermediates of glucose 6-phosphate and lysine led to the occurrence of an increase in plasmid DNA mutations (Table 7). Preliminary analysis of the mutated plasmids shows a predominance in plasmid deletions.

TABLE 7

INCREASED PLASMID MUTATION RATE WITH INCREASED GLUCOSE 6-PHOSPHATE-LYSINE INTERMEDIATE ADDITION

| % glucose | 6-phosphate-lysine | | intermediate | | (vol/vol) |
|---|---|---|---|---|---|
| | 50 | 25 | 12.5 | 5 | 0 |
| mutation rate | 149/2198 (0.0678) | 70/3428 (0.0204) | 23/3240 (0.0071)) | 74/3340 (0.0221) | 16/2235 (0.0071) |

EXAMPLE V

As noted above, the nonenzymatic glycosylation of plasmid DNA in vitro induces plasmid mutations when transformed into an appropriate bacterial host. In the present example, it is shown that a plasmid reacted with a protein structure modifying agent can also induce DNA mutations in the host genome.

MATERIALS AND METHODS

A filter sterilized solution of 1M glucose 6-phosphate, 10 mM lysine, 100 HEPES buffer, 1 mM EDTA was incubated for 4 days at 37° C. Following the incubation period, an equal volume of the solution was added to isolated plasmid DNA then incubated an additional 60 minutes at 37° C. Fifty nanograms of the reacted plasmid pBR322 DNA was used to transform competent K38 cells. The transformed cells were then grown on lactose indicator plates supplemented with 100 μg/ml. ampicillin. Those colonies which were unable to ferment lactose but ampicillin resistant were scored as genomic mutants.

RESULTS

Preliminary results have shown that the glucose 6-phosphate reactive intermediate need not be attached directly to the target DNA in order to induce mutations. We have shown the introduction of plasmid DNA, prepared as described in Example IV, can result in DNA damage to the host genome. A mutation rate for (lac+ to lac−) was found to be 1 in 35,000 transformants.

What is claimed is:

1. A method for preparing a protein of altered structure from target genetic material comprising:
    a. incubating a protein structure modifying agent comprising the reaction product of glucose-6-phosphate and an amino acid selected from the group consisting of lysine and putrescine with said target genetic material under conditions conducive for causing the reaction thereof;
    b. recovering any reacted genetic material from Step a. and introducing said reacted generic material into a bacterial cellular strain;

c. incubating the cellular strain of Step b. under conditions conductive to promoting mutation; and d. screening for and recovering genetic clones of the cellular strain of Step c. that provide a gene or protein material having an altered structure with the desired properties.

2. The method of claim 1, wherein said protein structure modifying agent is the reaction product of glucose 6-phosphate and lysine.

3. The method of claim 1, wherein said genetic material is DNA and said DNA is selected from the group consisting of plasmid DNA and phage DNA.

4. A method for preparing a protein of altered structure from nontarget genetic material comprising:

a. incubating a protein structure modifying agent comprising the reaction product of glucose-6-phosphate and an amino acid with said nontarget genetic material under conditions conducive for causing the reaction thereof;

b. recovering any reacted nontarget genetic material of Step a. and introducing said reacted nontarget genetic material into a distinct bacterial cellular host containing a target genetic material;

c. incubating the cellular host of Step b. containing said reacted nontarget genetic material of Step a. under conditions conducive for promoting mutation of the said target genetic material; and d. screening for and recovering those Step c. host cells that have modified genes or proteins resulting from the performance of Step a., b. and c. above.

5. The method of claim 4, wherein said protein structure modifying agent is the reaction product of glucose 6-phosphate and lysine.

6. The method of claim 4, wherein said genetic material is DNA and said DNA is selected from the group consisting of plasmid DNA and phage DNA.

7. The method of claim 4, wherein said target genetic material is endogenously present in said cellular host.

8. The method of claim 4, wherein said target genetic has been artificially introduced into said cellular host.

9. A method for preparing a protein of altered structure from target protein genetic material comprising:

a. locating a quantity of said target genetic material in a colony of bacterial cells selected from the group consisting of E coli strains DF2000 and DF40 that contain more of a protein structure modifying agent than wild type strain E. coli K10, said protein structure modifying agent comprising the reaction product of a glucose 6-phosphate and an amino acid selected from the group consisting of lysine and putrescine;

b. conducting an in vivo incubation of said target genetic material of said cells; and c. screening for and recovering genetic clones of the cells in Step b. that produce a protein material having an altered structure with the desired properties.

10. The method of claim 9, wherein said protein structure modifying agent is the reaction product of glucose 6-phosphate and lysine.

11. The method of claim 9, wherein said genetic material is DNA and said DNA is selected from the group consisting of plasmid DNA and phage DNA.

12. The method of claim 9, wherein said colony of cells is defective in at least one enzyme affecting the metabolism, elimination or generation of said protein structure modifying agents.

13. The method of claim 12, wherein said enzymes are selected from phosphoglucose isomerase and glucose 6-phosphate dehydrogenase.

14. The method of claim 9, wherein said colony of cells is derived from E. coli, is defective for phosphoglucose isomerase, and is identified as strain DF40.

15. The method of claim 9, wherein said colony of cells is derived from E. coli, is defective for phosphoglucose isomerase and glucose 6-phosphate dehydrogenase, and is identified as strain DF2000.

16. The method of claim 9, wherein said target genetic material is introduced into said colony of cells in Step a.

17. A method of preparing a protein of altered structure from target protein genetic material, comprising:

a. isolating a gene from an expression vector containing said genetic material;

b. incubating said gene with a protein structure modifying agent comprising the reaction product of glucose- 6-phosphate and an amino acid selected from the group consisting of lysine and putrescine to promote a reaction with said gene;

c. recovering any reacted genes resulting from the incubation of Step b.;

d. introducing the reacted gene of Step c. into a second expression vector; and e. using the expression vector of Step d. under conditions which promote mutation and thereby express a protein in the appropriate bacterial host, wherein the protein so expressed possesses said altered structure.

18. The method of claim 17, wherein said protein structure modifying agent is the reaction product of glucose 6-phosphate and lysine.

19. The method of claim 1, wherein said genetic material is DNA and said DNA is selected from the group consisting of plasmid DNA and phage DNA.

* * * * *